(12) United States Patent
Baynham et al.

(10) Patent No.: US 7,104,993 B2
(45) Date of Patent: Sep. 12, 2006

(54) CROSS LINK SYSTEM

(75) Inventors: Bret O. Baynham, Jupiter, FL (US); G. Clay Baynham, Jupiter, FL (US); Matthew G. Baynham, Jupiter, FL (US); David R. Campbell, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 172 days.

(21) Appl. No.: 10/776,732

(22) Filed: Feb. 10, 2004

(65) Prior Publication Data
US 2005/0177152 A1 Aug. 11, 2005

(51) Int. Cl.
*A61B 17/56* (2006.01)

(52) U.S. Cl. ...................................................... 606/61

(58) Field of Classification Search ................ 606/53, 606/54, 59, 61, 71, 72, 73
See application file for complete search history.

(56) References Cited

U.S. PATENT DOCUMENTS

| 5,275,600 | A | | 1/1994 | Allard et al. | |
|---|---|---|---|---|---|
| 5,693,053 | A | | 12/1997 | Estes | |
| 5,702,393 | A | * | 12/1997 | Pfaifer | 606/61 |
| 5,928,233 | A | * | 7/1999 | Apfelbaum et al. | 606/61 |
| 5,947,966 | A | * | 9/1999 | Drewry et al. | 606/61 |
| 6,010,503 | A | * | 1/2000 | Richelsoph et al. | 606/61 |
| 6,283,967 | B1 | | 9/2001 | Troxell et al. | |
| 6,302,882 | B1 | | 10/2001 | Lin et al. | |
| 6,306,137 | B1 | | 10/2001 | Troxell | |
| 6,524,315 | B1 | * | 2/2003 | Selvitelli et al. | 606/70 |
| 6,602,253 | B1 | | 8/2003 | Richelsoph et al. | |
| 6,736,817 | B1 | | 5/2004 | Troxell et al. | |
| 6,761,721 | B1 | | 7/2004 | Burgess et al. | |
| 6,887,241 | B1 | * | 5/2005 | McBride et al. | 606/61 |
| 2002/0111625 | A1 | | 8/2002 | Richelsoph et al. | |
| 2003/0114853 | A1 | | 6/2003 | Burgess et al. | |
| 2003/0153917 | A1 | | 8/2003 | Richelsoph et al. | |
| 2004/0116928 | A1 | * | 6/2004 | Young et al. | 606/601 |
| 2004/0133203 | A1 | | 7/2004 | Young et al. | |

* cited by examiner

*Primary Examiner*—Corrine McDermott
*Assistant Examiner*—William H Matthews
(74) *Attorney, Agent, or Firm*—McHale & Slavin PA

(57) ABSTRACT

A cross link system provides stability to spinal rods by maintaining a set distance between the rods. The cross link has a bar with connectors on each end formed with grooves that engage each of the spinal rods. Each of the connectors has a cam that can be manipulated to obstruct the groove and provide a friction fit between the spinal rod and the cross link. The cams have locking nuts that prevent disengagement of the cam and rod. The bar has two shafts interconnected by a bifurcated pin with upstanding ends, a piston is located between the upstanding ends and diverts shear forces along the longitudinal axis of the bar.

4 Claims, 3 Drawing Sheets

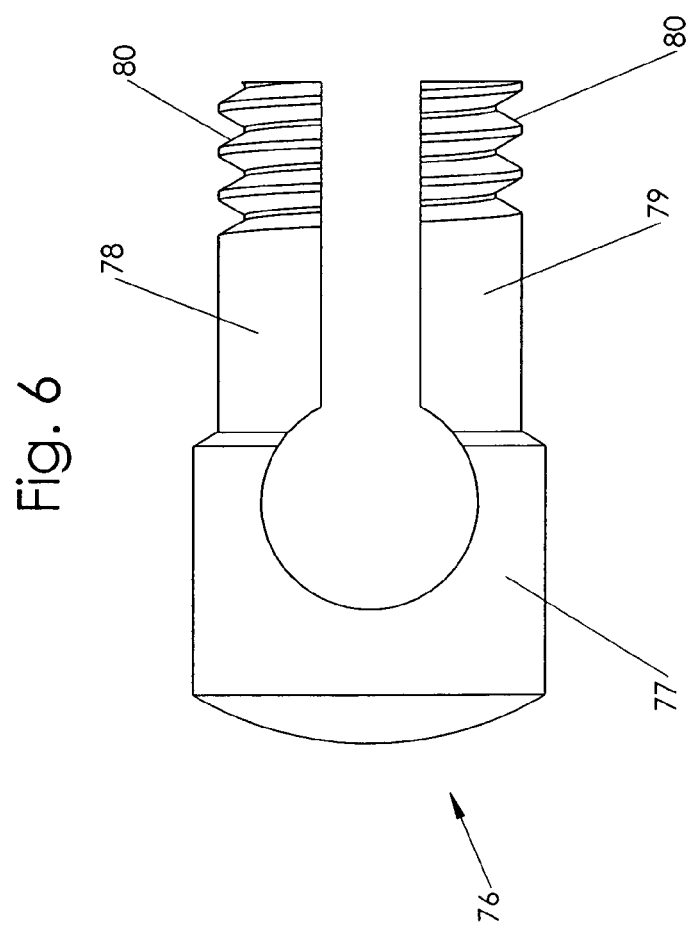
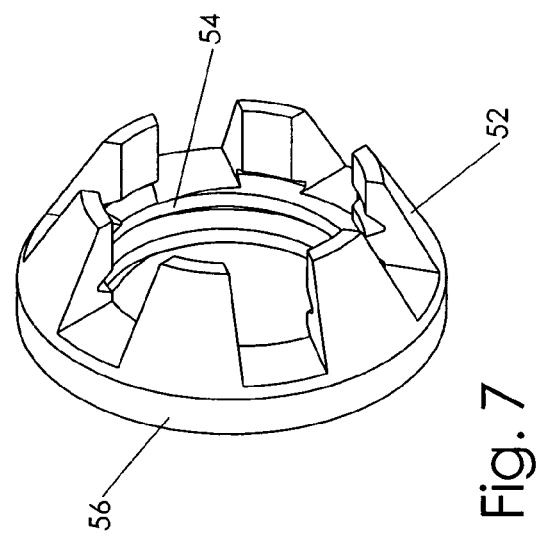

CROSS LINK SYSTEM

BACKGROUND OF THE INVENTION

1. Field of the Invention

This invention relates to the field of orthopedic surgery and, particularly, to a cross link attachable to a pair of spinal rods to stabilize relative movement between the rods during body movements.

2. Description of the Prior Art

The use of spinal rods is conventional for correction of spinal trauma or conditions, such as curvature of the spine. Generally parallel rods are attached to the spine by pedicle screws for support or correction of abnormalities. During normal activities, the spine is subjected to bending and twisting motions which affect the relative position of the spinal rods. In some cases, the rods are cross braced for additional stability. The cross link is attached to each of the spinal rods and provides fixed spacing between the rods. The resultant forces acting on the cross link are primarily in shear along the longitudinal axis of the cross link.

Estes, U.S. Pat. No. 5,693,053, teaches the use of a rigid cross link with an eye on each end. The eyes are oblong to provide some adjustability in length of the cross link. Bolts connected to the spinal rods are passed through the eyes. Nuts are then applied to hold the assembly in place. The shear forces tend to cause the bolts to move within the oblong eyes.

U.S. Pat. No. 5,275,600 to Allard et al teaches a two piece cross link with telescoping members. Each end of the two piece rod has a hook for engaging the spinal rods. Each hook has a downwardly facing opening in which the spinal rod is captured. The opposing sides of the hook resist the shear forces however, there is nothing to prevent the hooks from, "walking," along the spinal rods in response to unequal movement of each spinal rod. The other end of one rod is telescoped into the second rod. A set screw is threaded through the telescoped portions engaging both members and fixing the length of the cross link. The set screw is threaded through the exterior rod and the interior rod has a hook or flange to prevent separation. The ends of the telescoped rods act directly on the shaft of the set screw in shear which may result in deformation or failure.

Lin et al, U.S. Pat. No. 6,302,882, teach a cross link with two shafts that overlap each other. Each shaft has a double hook on one end for engaging a spinal rod. The double hook enlarges the contact area between the cross link and the spinal rods to resist, "walking," along the spinal rods. The other ends of the shafts each have a reduced thickness and are overlapped. A clip or sleeve is placed over the overlapped portions. The clip has a smaller diameter than the diameter of the overlapped portions which creates a force fit. A set screw may be used to secure the clip on the overlapped shafts. The shear forces can move the overlapped portions within the clip since there is no transverse fastening in the assembly.

Because of the forces acting along the cross link and the movement of the spinal rods, the connection between the cross link and the spinal rod must be secure to avoid movement of the cross link along the spinal rod. Further, the connection between multi-shaft cross links must resist shear to avoid separation, in the worst case, and to provide stability to the spinal rods.

SUMMARY OF THE PRESENT INVENTION

Therefore, it is an objective of this invention to provide a cross link system for spinal rods that is positively secured along the length of each spinal rod.

It is another objective of this invention to provide a cross link system having two inter-engaged shafts which divert shear forces.

It is a further objective of this invention to provide a pin connecting the inter-engaged shafts that is isolated from shear forces along the shafts.

It is yet another objective of this invention to provide a cross link system with cams to engage spinal rods.

It is still another objective of this invention to provide a key to lock the cams in engagement with the spinal rods.

SHORT DESCRIPTION OF THE DRAWINGS

FIG. 6 is a perspective of the key of this invention; and

FIG. 7 is a side view of the pin of this invention.

DETAILED DESCRIPTION OF THE INVENTION

Figure 1:
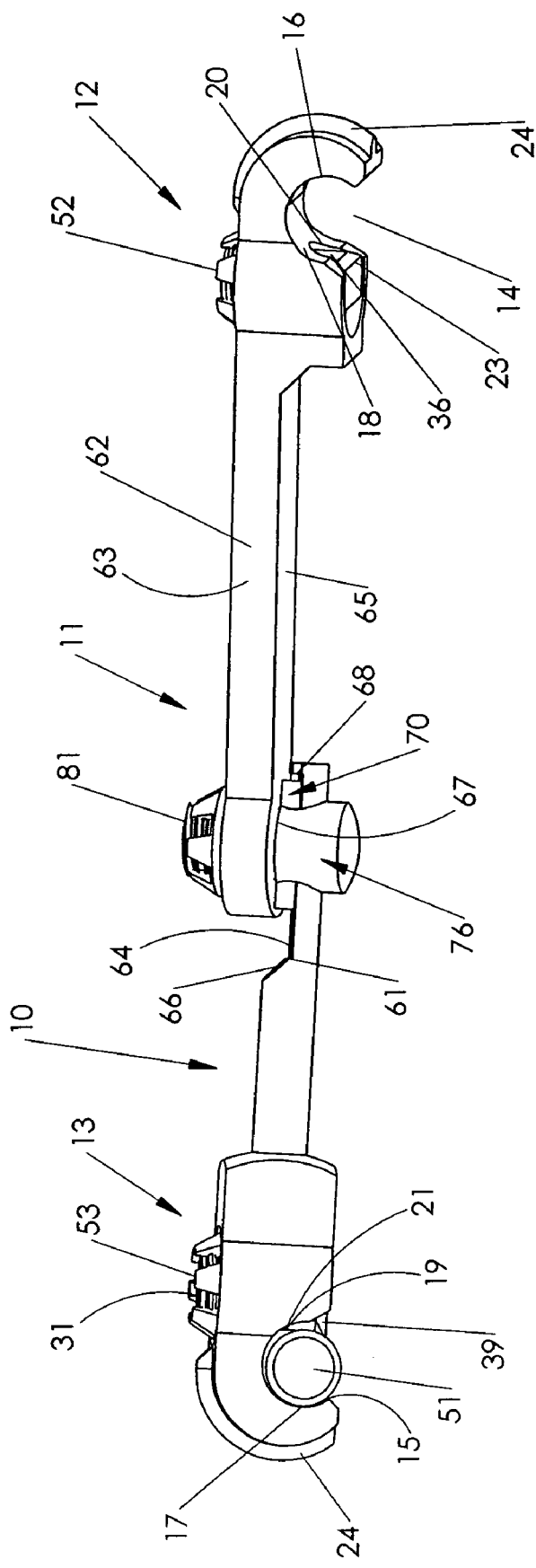
FIG. 1 is a perspective of the cross link system of this invention.

The link system 10 has a bar 11 which extends between two generally parallel spinal rods, only rod 51 is shown. The bar 11 has two connectors 12 and 13 that are placed over the rods to hold the cross link in place along the length of the rods. Connector 12 has a groove 14 which is transverse to the longitudinal axis of the bar 11. The groove 14 has upstanding sides 16 and 18. A channel 20 is formed in upstanding wall 18. The channel 20 is a discontinuity in the side wall 18 and exposes a portion of the actuator arm 23. The upstanding wall 16 is reinforced with a thickened ridge 24 along the outer surface of the groove 14.

Connector 13 has a groove 15 which is transverse to the longitudinal axis of the bar 11. The groove 15 has upstanding sides 17 and 19. A channel 21 is formed in upstanding wall 19. The channel 21 is a discontinuity in the side wall 19 and exposes a portion of the actuator arm 23. The upstanding wall 17 is reinforced with a thickened ridge along the outer surface of the groove 15.

Figure 2:
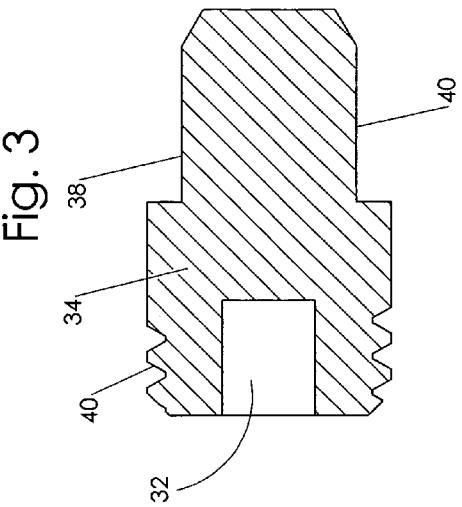
FIG. 2 is a perspective of a lock of cross link system.
Figure 3:
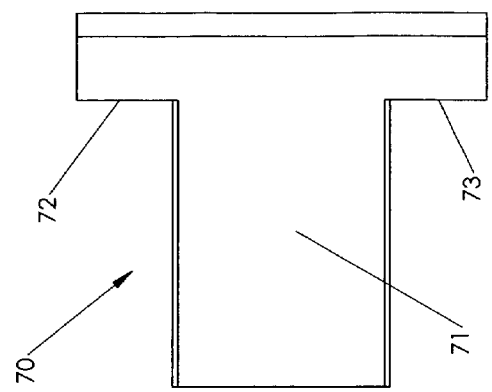
FIG. 3 is a cross section of FIG. 2 along line A—A.

The lock 30, shown in FIG. 2, is rotatably mounted in the connector 12 and extends along the upstanding wall 18. The lock has external threads 40 about the upper periphery. The lock is operated by a tool (not shown) that is shaped to fill the slot 32 in the top of the lock. As the tool is rotated, the lock rotates in the longitudinal axis. The body of the lock is an actuator arm 34 which has a cam surface 36. As shown, the cam surface 36 is formed by opposed planar surfaces 38, 40 of reduced diameter. Of course only one planar surface may be used. However, when the groove 14 is unobstructed, a planar surface is exposed in the channel 20. Upon rotation of the actuator arm 90 degrees the cam surface 36 swings into the groove to obstruct passage and positively engage a spinal rod.

The end of the lock opposite the slot 32 has a retainer 39 formed as a flange on the cam surface. As the cam 36 engages the spinal rod the retainer rotates under the spinal rod preventing displacement of the rod from the groove 14.

The lock 31, shown in FIG. 1, is rotatably mounted in the connector 13 and extends along the upstanding wall 19. The lock 31 is operated as is the lock 30. The body of the lock is formed as is the lock 30. However, when the groove 15 is unobstructed, a planar surface is exposed in the channel. Upon rotation of the actuator arm 90 degrees the cam surface swings into the groove to obstruct passage and positively engage a spinal rod and the retainer 39 slides under the spinal rod.

Each lock 30 and 31 has a key 52 and 53, shown in detail in FIG. 7, to prevent the disengagement of the cam from the spinal rod. The key 52 has threads 54 for connecting with the threads on the lock 30. An enlarged head 56 forms a reaction surface with the connector 12 to apply compression between the head, the retainer and the spinal rod for an interference fit.

The bar 11 has two shafts 61 and 62 which are interconnected to establish the spatial relationship between the spinal rods. Shaft 61 is rigidly connected to and extends from connector 13 normal to the upstanding walls 17 and 19. As shown in FIG. 1, the shaft 62 has planar surfaces 63 and 65 though the shape may be other than rectangular cross section. A bore 67 is located near the end of the shaft 62.

The shaft 62 is rigidly connected to and extends from connector 12 normal to the upstanding walls 16 and 18. As shown in FIG. 1, the shaft 61 is round though the shape may have another cross section. Near the end of the shaft 61 there is a reduced diameter portion 64 defined by an inner shoulder 66 and an outer shoulder 68 forming the end of the shaft.

Figure 4:
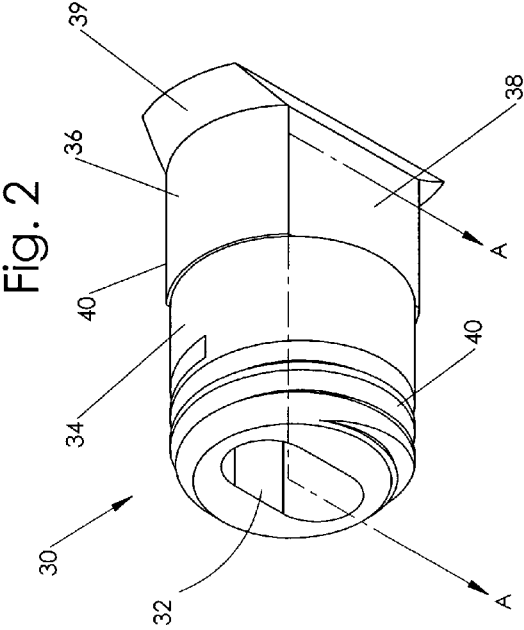
FIG. 4 is a top plan view, partially in section, of the pin and the piston of the cross link system.
Figure 5:
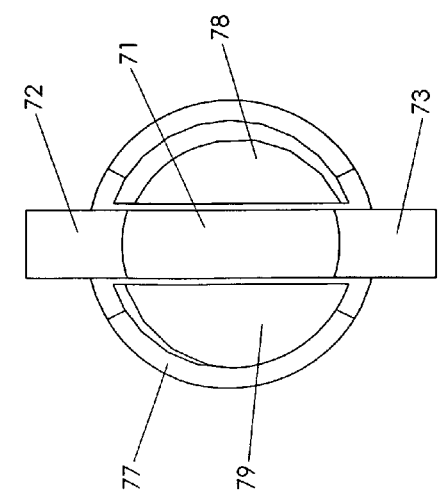
FIG. 5 is a cross section of the piston of this invention.

A piston 70, shown in FIGS. 4 and 5, has a body 71 of such dimensions to be inserted into bore 67. On one end of the piston body 71 diametrically opposed flanges 72 and 73 extend beyond the thickness of the body. The flanges 72 and 73 have a width commensurate with the diameter of the shaft 61. In operation, the flanges 72 and 73 contact the reduced thickness portion 64 of the shaft and the ends 74 and 75 cooperate with shoulders 66 and 68 to divert shear forces acting along the longitudinal axis of bar 11.

A bifurcated pin 76, shown in FIG. 6, has an enlarged head 77 and upstanding ends 78,79. The upstanding ends are separated by a distance to allow the reduced diameter portion of end of shaft 61 and the piston 70 to be disposed therebetween, as shown in FIG. 4. The upstanding ends 78, 79 may have external threads 80, or be internally threaded or both. The pin 76 and the piston 70 may be pre-assembled with the shaft 62 for simplicity and to reduce the number of separate components within the surgical field.

Once the shafts 61 and 62 are overlapped, the pin 76 and piston 70 are inserted into bore 67 and a fastener 81 is connected to the upstanding ends 78 and 79 to complete the assembly of the cross link system. The fastener 81 is similar in construction to key 52. However, the fastener may be internally threaded, as shown, or externally threaded to mate with threads on the upstanding ends and/or with internal threads in the bore 67.

The connection of the shafts 61 and 62 is such that the bar 11 may not be straight between the spinal rods. Also, the bar can rotate, to some degree, in the longitudinal axis. Lateral movement along the longitudinal axis is limited by the flanges contacting the shoulder of the shaft 62. Because the flanges are 90 degrees from the upstanding ends of the pin, about the circumference of the piston, the shear forces act through the flanges against the bore and isolate the pin.

A number of embodiments of the present invention have been described. Nevertheless, it will be understood that various modifications may be made without departing from the spirit and scope of the invention. Accordingly, it is to be understood that the invention is not to be limited by the specific illustrated embodiment but only by the scope of the appended claims.

We claim:

1. A cross link system for stabilizing and connecting a pair of spinal rods comprising a bar having a longitudinal axis with a first connector on one end and a second connector on the other end, said first connector having a first groove transverse to said longitudinal axis of said bar for passage of a spinal rod, a first lock mounted on said first connector with a first actuator arm adapted to extend into said first groove, said first arm movable to obstruct said first groove to frictionally engage said first connector and one of the spinal rods, said second connector having a second groove transverse to said longitudinal axis of said bar for passage of another spinal rod, said bar comprises a first shaft and a second shaft, said first shaft and said second shaft joined by a pin, said pin having a U-shape with upstanding free ends supporting a portion of said first shaft, said second shaft having a bore, said free ends of said pin passing through said bore, a fastener engaging said free ends and said bore securing said pin and said first shaft and said second shaft together, said first shaft has a portion of reduced thickness along said longitudinal axis adjacent to said bore in said second shaft, said reduced thickness defined by a shoulder on each end, a piston located in said reduced thickness and extending into said bore, said piston having opposed flanges extending along said reduced thickness, said flanges adapted to contact said shoulders during relative movement of said first shaft and said second shaft in said longitudinal axis and translate shear forces to said piston.

2. A cross link system for stabilizing and connecting a pair of spinal rods comprising a bar having a longitudinal axis with a first connector on one end and a second connector on the other end, said first connector having a first groove transverse to said longitudinal axis of said bar for passage of a spinal rod, a first lock mounted on said first connector with a first actuator arm adapted to extend into said first groove, said first arm movable to obstruct said first groove to frictionally engage said first connector and one of the spinal rods, said second connector having a second groove transverse to said longitudinal axis of said bar for passage of another spinal rod, a second lock is mounted on said second connector with a second actuator arm adapted to extend into said second groove, said second arm shaped to obstruct said second groove to frictionally engage said second connector and another of the spinal rods, said bar comprises a first shaft and a second shaft, said first shaft and said second shaft joined by a pin, said pin having a U-shape with upstanding free ends supporting a portion of said first shaft, said second shaft having a bore, said free ends of said pin passing through said bore, a fastener engaging said free ends and said bore securing said pin and said first shaft and said second shaft together, said first shaft has a portion of reduced thickness along said longitudinal axis adjacent to said bore in said second shaft, said reduced thickness defined by a shoulder on each end, a piston located in said reduced thickness and extending into said bore, said piston having opposed flanges extending along said reduced thickness, said flanges adapted to contact said shoulders during relative movement of said first shaft and said second shaft in said longitudinal axis and translate shear forces to said piston.

3. A cross link system for stabilizing and connecting a pair of spinal rods comprising a bar having a longitudinal axis with a first connector on one end and a second connector on the other end, said first connector having a first groove transverse to said longitudinal axis of said bar for passage of a spinal rod, a first lock mounted on said first connector with a first actuator arm adapted to extend into said first groove, said first arm movable to obstruct said first groove to frictionally engage said first connector and one of the spinal rods, said second connector having a second groove transverse to said longitudinal axis of said bar for passage of another spinal rod, a second lock is mounted on said second connector with a second actuator arm adapted to extend into said second groove, said second arm shaped to obstruct said second groove to frictionally engage said second connector and another of the spinal rods, said bar comprises a first shaft and a second shaft, said first shaft and said second shaft joined by a pin, said pin having a U-shape with upstanding free ends supporting a portion of said first shaft, said second shaft having a bore, said free ends of said pin passing through said bore, a fastener engaging said free ends and said bore securing said pin and said first shaft and said second shaft together, a piston located between said upstanding free ends and extending into said bore, said piston having opposed flanges extending along said first and second shaft, said first shaft has a portion of reduced thickness along said longitudinal axis adjacent to said bore in said second shaft, said reduced thickness defined by a shoulder on each end, said piston located in said reduced thickness and extending into said bore, said flanges adapted to contact said shoulders during relative movement of said first shaft and said second shaft in said longitudinal axis and translate shear forces to said piston.

4. A cross link system of claim 3 wherein a first key is movably mounted on said first connector in contact with said first lock, said first key blocking said first actuator arm from disengagement when said first actuator arm obstructs said first groove, a second key is movably mounted on said second connector in contact with said second lock, said second key blocking said second actuator arm from disengagement when said second actuator arm obstructs said second groove.

\* \* \* \* \*